(12) United States Patent
Grady et al.

(10) Patent No.: US 12,310,759 B2
(45) Date of Patent: May 27, 2025

(54) SYSTEMS AND METHODS FOR DIAGNOSIS, RISK ASSESSMENT, AND/OR VIRTUAL TREATMENT ASSESSMENT OF VISCERAL ISCHEMIA

(71) Applicant: HeartFlow, Inc., Redwood City, CA (US)

(72) Inventors: Leo J. Grady, Millbrae, CA (US); Charles A. Taylor, Menlo Park, CA (US); Christopher K. Zarins, Menlo Park, CA (US)

(73) Assignee: Heartflow, Inc., Mountain View, CA (US)

( * ) Notice: Subject to any disclaimer, the term of this patent is extended or adjusted under 35 U.S.C. 154(b) by 476 days.

(21) Appl. No.: 14/994,555

(22) Filed: Jan. 13, 2016

(65) Prior Publication Data
US 2016/0224753 A1    Aug. 4, 2016

Related U.S. Application Data

(60) Provisional application No. 62/110,802, filed on Feb. 2, 2015.

(51) Int. Cl.
*A61B 5/00* (2006.01)
*A61B 5/021* (2006.01)
(Continued)

(52) U.S. Cl.
CPC ............ *A61B 5/7275* (2013.01); *A61B 5/021* (2013.01); *A61B 5/026* (2013.01); *A61B 5/4255* (2013.01);
(Continued)

(58) Field of Classification Search
CPC ....... A61B 5/7275; A61B 5/029; A61B 5/021; A61B 5/0044; A61B 2576/023;
(Continued)

(56) References Cited

U.S. PATENT DOCUMENTS 10,456,094 B2 * 10/2019 Fonte ..................... A61B 6/032
2005/0187469 A1 * 8/2005 Phillips ................ A61B 5/1455
600/437
(Continued)

FOREIGN PATENT DOCUMENTS

CN        104 107 039 A     10/2014

OTHER PUBLICATIONS

Joyner MJ, Casey DP. Regulation of Increased Blood Flow (Hyperemia) to Muscles During Exercise: A Hierarchy of Competing Physiological Needs. Physiological Reviews. 2015;95(2):549-601 at pp. 556-557 (Joyner)).*
(Continued)

*Primary Examiner* — Eric J Messersmith
*Assistant Examiner* — Kyle W. Kretzer
(74) *Attorney, Agent, or Firm* — Bookoff McAndrews, PLLC

(57) ABSTRACT

Systems and methods are disclosed for diagnosis, risk assessment, and/or virtual treatment assessment of visceral ischemia and related disorders. One method includes receiving a patient-specific anatomic model of a patient's visceral vasculature, including visceral vasculature of the patient's visceral organs and bowel; determining a location in the patient-specific anatomic model of the patient's visceral vasculature; determining, for the location in the patient-specific anatomic model, a blood flow characteristic of blood flow through the location in the patient-specific anatomic model of the patient's visceral vasculature; determining a tissue region of the patient's bowel proximate the location in the patient-specific anatomic model of the patient's visceral vasculature; and generating an assessment of blood supply adequacy to the tissue region of the patient's bowel or generating a risk score for risk of disease for the patient's bowel, based on the determined blood flow char-
(Continued)

acteristic and an expected blood flow characteristic associated with the tissue region of the patient's bowel.

20 Claims, 6 Drawing Sheets

(51) Int. Cl.
  *A61B 5/026*   (2006.01)
  *G16H 50/30*   (2018.01)
  *G16H 50/50*   (2018.01)
  *G16Z 99/00*   (2019.01)
(52) U.S. Cl.
  CPC ........... *A61B 5/7425* (2013.01); *G16H 50/30* (2018.01); *G16H 50/50* (2018.01); *G16Z 99/00* (2019.02); *A61B 5/0022* (2013.01); *A61B 5/489* (2013.01)
(58) Field of Classification Search
  CPC ......... A61B 5/00; A61B 5/026; A61B 5/4255; A61B 5/7425; A61B 5/489; A61B 5/0022; G06F 19/3437; G06F 19/3431; G06F 19/00; G16Z 99/00; G16H 50/50; G16H 50/30
  USPC ...................................... 600/485, 504; 703/2
  See application file for complete search history.

(56) References Cited

U.S. PATENT DOCUMENTS

| | | | | |
|---|---|---|---|---|
| 2007/0208263 | A1* | 9/2007 | John ....................... | A61B 5/349 600/509 |
| 2012/0041318 | A1* | 2/2012 | Taylor .................... | G06T 17/005 703/11 |
| 2012/0088955 | A1* | 4/2012 | Taub .................... | A61M 1/3653 600/16 |
| 2014/0073976 | A1 | 3/2014 | Fonte et al. | |
| 2014/0107935 | A1* | 4/2014 | Taylor ...................... | G06K 9/52 702/19 |
| 2014/0355859 | A1 | 12/2014 | Taylor et al. | |
| 2016/0106347 | A1* | 4/2016 | Patwardhan .......... | G06T 7/0012 600/407 |
| 2018/0192873 | A1* | 7/2018 | Chausiaux ........... | A61B 5/6831 |

OTHER PUBLICATIONS

T. Mabotuwana, L. Cheng, and A Pullan, "A model of blood flow in the mesenteric arterial system" Biomed Eng Online. 2007 (Mabotuwana).*

Walker, T Gregory. "Mesenteric vasculature and collateral pathways" Seminars in interventional radiology vol. 26, 3 (2009): 167-74 (Walker) (Year: 2009).*

Hoffman, M, "Picture of the Intestines" Human Anatomy, WebMD, https://www.webmd.com/digestive-disorders/picture-of-the-intestines#1 (Year: 2017).*

Heldt, T., and R. G. Mark. "Scaling cardiovascular parameters for population simulations." Computers in Cardiology, 2004. IEEE, 2004 (Year: 2004).*

Cleveland Clinic "Intestinal Ischemic Syndrome" (Year: 2016).*

Mabotuwana T D S et al.: "Modeling Blood Flow in the Gastrointestinal System", Conference Proceedings. Annual International Conference of the IEEE Engineering in Medicine and Biology Society (IEEE Cat. No. 06CH37748); Aug. 30-Sep. 3, 2006; New York, NY, USA, IEEE, Piscataway, NJ, USA Aug. 30, 2006 (Aug. 30, 2006), pp. 1810-1813.

International Search Report and Written Opinion for corresponding Application No. PCT/US2016/015925 dated May 4, 2016, (13 pages).

Seike, Kazuhiro, et al. "Laser Doppler assessment of the influence of division at the root of the inferior mesenteric artery on anastomotic blood flow in rectosigmoid cancer surgery." International journal of colorectal disease 22.6 (2007): 689-697 (Seike).

* cited by examiner

SYSTEMS AND METHODS FOR DIAGNOSIS, RISK ASSESSMENT, AND/OR VIRTUAL TREATMENT ASSESSMENT OF VISCERAL ISCHEMIA

RELATED APPLICATION(S)

This application claims priority to U.S. Provisional Application No. 62/110,802 filed Feb. 2, 2015, the entire disclosure of which is hereby incorporated herein by reference in its entirety.

FIELD OF THE DISCLOSURE

Various embodiments of the present disclosure relate generally to disease assessment, treatment planning, and related methods. More specifically, particular embodiments of the present disclosure relate to systems and methods for performing diagnosis, risk assessment, and/or virtual treatment assessment of visceral ischemia.

BACKGROUND

Various parts of vessels in the human body may experience high degrees of vascular collateralization, including the growth of one or more blood vessels that serve the same areas of anatomy. In some cases, collateralization may occur where blood supply to an area of anatomy is adequate, for instance, in the abdomen, rectum, knee, shoulder, and head. Such collateralization may offer advantages in surgery, by acting as a protective measure to provide adequate supply of blood. In other scenarios, collateralization may occur where blood supply to the area of anatomy is inadequate, in which case, collateralization may partly compensate for blood vessel(s) that do not supply the area of anatomy sufficiently.

The mixing of blood sources due to collateralization may interfere with the detection of non-functioning or diseased vessels. For example, collateralization may hinder determinations of whether vascular disease is functionally significant. For instance, the heavy amount of collateralization in visceral vasculature compromises detection of vascular disease in visceral vasculature that may cause ischemia (e.g., resulting in visceral ischemia).

Visceral ischemia (including mesenteric ischemia, intestinal ischemia, visceral angina, ischemic colitis, etc.) and related disorders may be difficult to diagnose and differentiate from other causes of abdominal pain. The diagnosis may be especially difficult to make early, before symptoms have severely progressed. While various imaging techniques may permit examination of visceral vasculature, collateralization may interfere with the ability to determine functional significance of vascular disease from imaging alone.

This disclosure includes systems and methods for diagnosing visceral ischemia and related disorders, and determining an optimal treatment for a patient. The foregoing general description and the following detailed description are exemplary and explanatory only and are not restrictive of the disclosure.

SUMMARY

According to certain aspects of the present disclosure, systems and methods are disclosed for diagnosis, risk assessment, and/or virtual treatment assessment of visceral ischemia.

One method includes: receiving a patient-specific anatomic model of a patient's visceral vasculature, including visceral vasculature of the patient's visceral organs and bowel; determining a location in the patient-specific anatomic model of the patient's visceral vasculature; determining, for the location in the patient-specific anatomic model, a blood flow characteristic defining a characteristic of blood flow through the location in the patient-specific anatomic model of the patient's visceral vasculature; determining a tissue region of the patient's bowel distal to the location in the patient-specific anatomic model of the patient's visceral vasculature; and generating an assessment of blood supply adequacy defining an adequacy of blood supply to the tissue region of the patient's viscera or bowel, or generating a risk score defining a risk of disease of the patient's viscera or bowel, based on the determined blood flow characteristic and an expected blood flow characteristic associated with the tissue region of the patient's bowel.

In accordance with another embodiment, a system for assessment of visceral ischemia and related disorders comprises: a data storage device storing instructions for assessment of visceral ischemia and related disorders; and a processor configured for: receiving a patient-specific anatomic model of a patient's visceral vasculature, including visceral vasculature of the patient's visceral organs and bowel; determining a location in the patient-specific anatomic model of the patient's visceral vasculature; determining, for the location in the patient-specific anatomic model, a blood flow characteristic defining a characteristic of blood flow through the location in the patient-specific anatomic model of the patient's visceral vasculature; determining a tissue region of the patient's bowel distal to the location in the patient-specific anatomic model of the patient's visceral vasculature; and generating an assessment of blood supply adequacy defining an adequacy of blood supply to the tissue region of the patient's viscera or bowel, or generating a risk score defining a risk of disease of the patient's viscera or bowel, based on the determined blood flow characteristic and an expected blood flow characteristic associated with the tissue region of the patient's bowel.

In accordance with another embodiment, a non-transitory computer readable medium for use on a computer system containing computer-executable programming instructions for assessment of visceral ischemia and related disorders, the method comprising: receiving a patient-specific anatomic model of a patient's visceral vasculature, including visceral vasculature of the patient's visceral organs and bowel; determining a location in the patient-specific anatomic model of the patient's visceral vasculature; determining, for the location in the patient-specific anatomic model, a blood flow characteristic defining a characteristic of blood flow through the location in the patient-specific anatomic model of the patient's visceral vasculature; determining a tissue region of the patient's bowel distal to the location in the patient-specific anatomic model of the patient's visceral vasculature; and generating an assessment of blood supply adequacy defining an adequacy of blood supply to the tissue region of the patient's viscera or bowel, or generating a risk score defining a risk of disease of the patient's viscera or bowel, based on the determined blood flow characteristic and an expected blood flow characteristic associated with the tissue region of the patient's bowel.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Visceral ischemia and related disorders are a relatively common cause of hospital admissions. For example, ischemic colitis may lead to bowel perforation or sepsis, both of which may be deadly. Although visceral ischemia and related disorders may be seen on about one in about one hundred endoscopies, visceral ischemia and related disorders may be difficult to diagnose and differentiate from other causes of abdominal pain. The diagnosis may be especially difficult to make early, before symptoms have severely progressed. One reason for the difficulty in earlier diagnosis is collateralization within visceral vasculature.

For example, the heavy amount of collateralization in the visceral vasculature makes it challenging to determine, from imaging alone, whether vascular disease is functionally significant (e.g., causing ischemia). Noninvasive imaging techniques, e.g., contrast computed tomography ("CCT") and/or magnetic resonance imaging ("MRI") may provide a means to examine a visceral vasculature. Meanwhile, recent advances in image analytics techniques may improve the accuracy of models (e.g., blood flow models) of the visceral vasculature and bowel tissue (e.g., see T. Mabotuwana, L. Cheng, and A. Pullan, "A model of blood flow in the mesenteric arterial system" Biomed Eng Online. 2007, which teaches modeling blood flow in the visceral vasculature and focuses on verifying production of realistic flow profiles). A desire exists to leverage advances in blood flow simulation to use the advances in conjunction with improved imaging of patient anatomy. A desire also exists to perform blood flow simulations involving more than mere simplistic fluid simulation assumptions, for example, by accounting for the blood flow demand by the bowel. A desire further exists to assess the functional significance of visceral vascular disease, e.g., based on the blood flow simulations.

The present disclosure describes systems and methods for diagnosing visceral ischemia and determining an optimal treatment for a patient, e.g., via blood flow simulations through patient-specific models built from images of patient anatomy. Visceral ischemia and related disorders may include mesenteric ischemia, intestinal ischemia, ischemic colitis, disorders related to a patient's celiac artery, etc.

Figure 1:
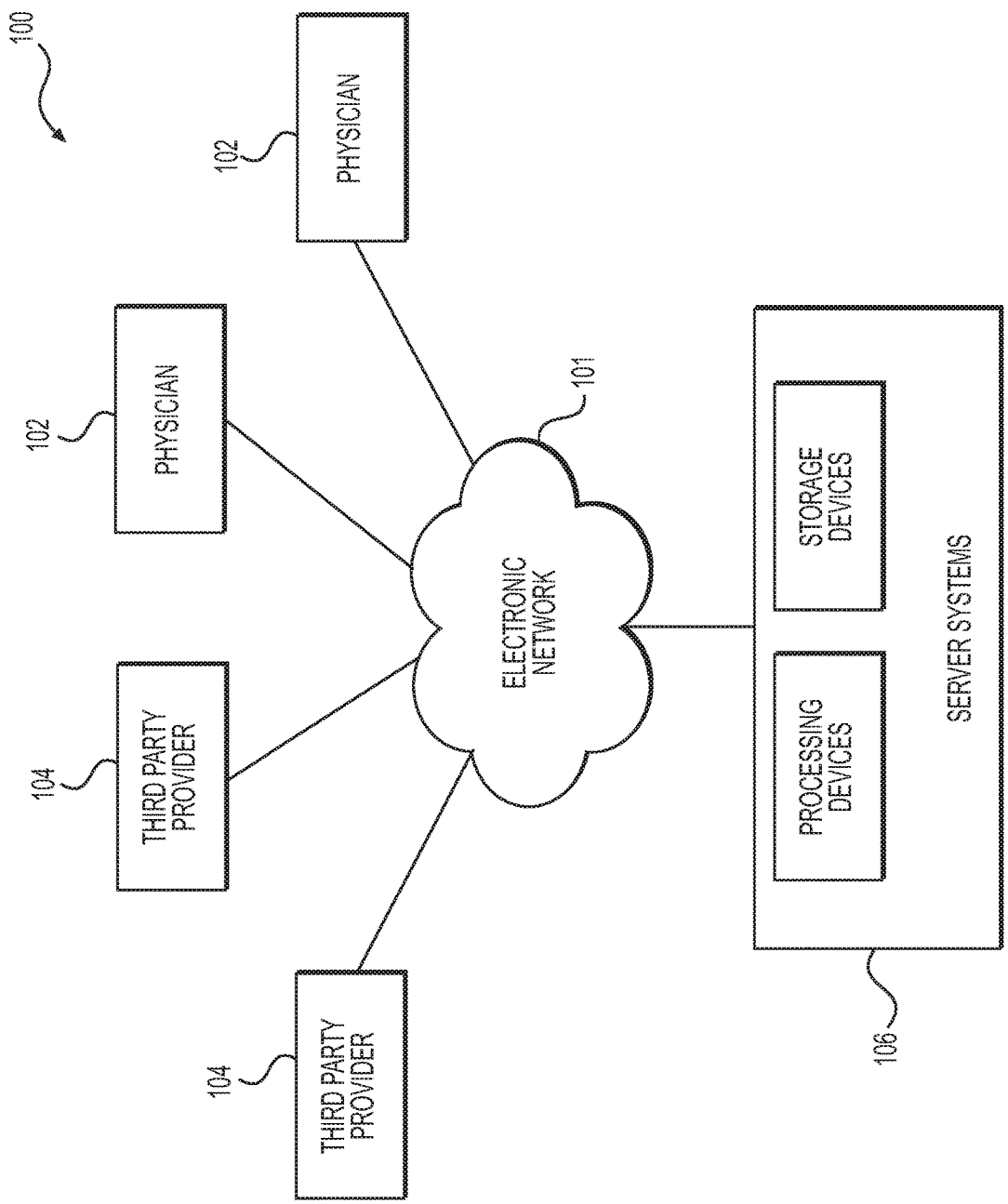
FIG. 1 is a block diagram of an exemplary system and network for diagnosis, risk assessment, and/or virtual treatment assessment of visceral ischemia, according to an exemplary embodiment of the present disclosure.

Referring now to the figures, FIG. 1 depicts a block diagram of an exemplary system 100 and network for diagnosis, risk assessment, and/or virtual treatment assessment of visceral ischemia, according to an exemplary embodiment. Specifically, FIG. 1 depicts a plurality of physicians 102 and third party providers 104, any of whom may be connected to an electronic network 101, for example, the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomic images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices. For the purposes of the disclosure, "patient" may refer to any individual or person for whom diagnosis or treatment analysis is being performed, or any individual or person associated with the diagnosis or treatment analysis of one or more individuals.

Figure 2A:
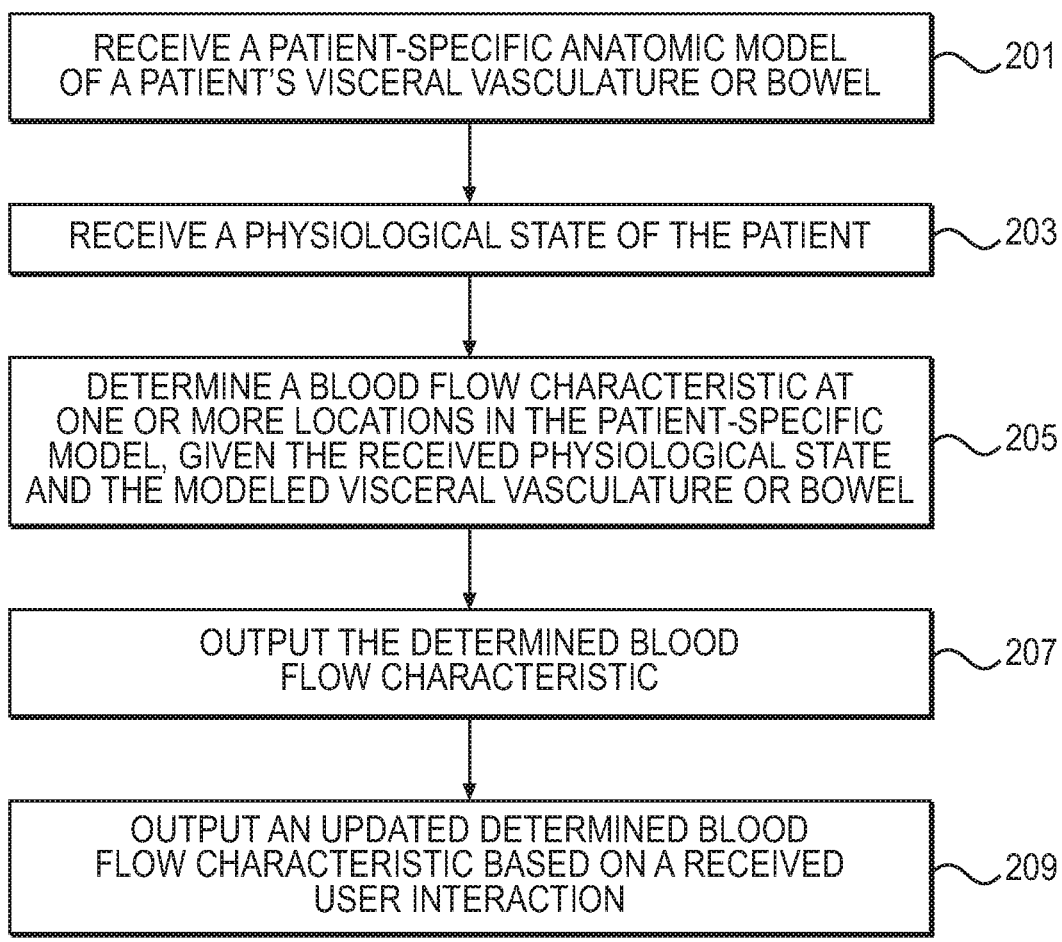
FIG. 2A is a flow diagram of an exemplary method of determining blood flow characteristics through a patient's visceral vasculature or bowel, according to an exemplary embodiment of the present disclosure.
Figure 2B:
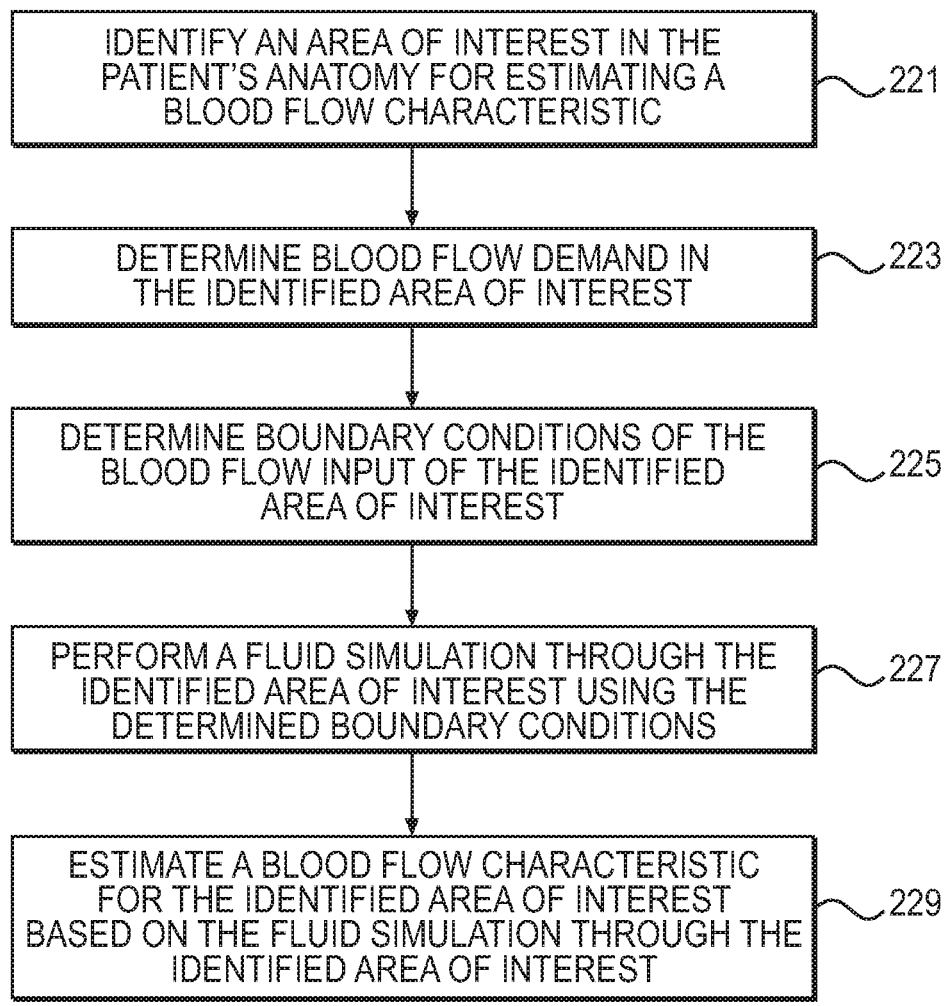
FIG. 2B is a flow diagram of an exemplary method of determining a blood flow characteristic at one or more locations in a patient-specific vascular model using simulation, according to an exemplary embodiment of the present disclosure.
Figure 2C:
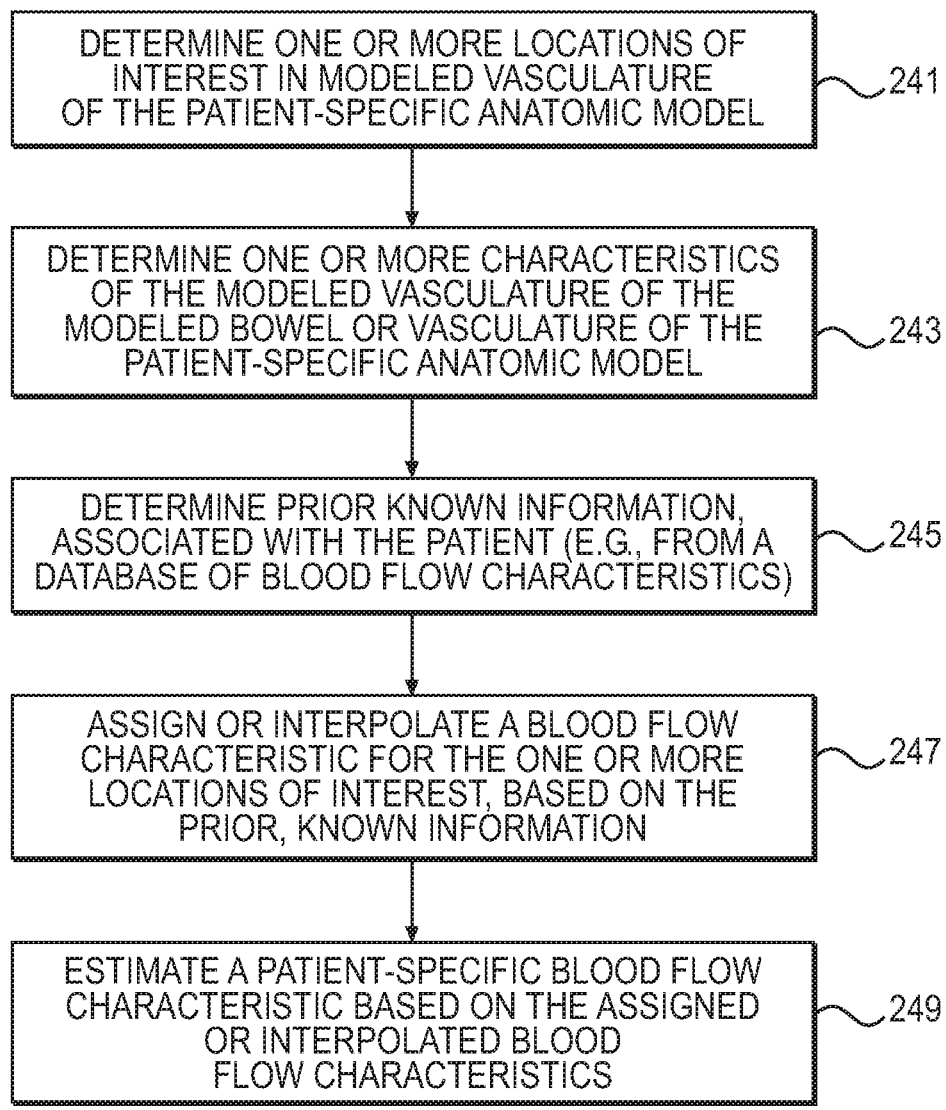
FIG. 2C is a flow diagram of an exemplary method of determining a blood flow characteristic at one or more locations in a patient-specific model using machine learning, according to an exemplary embodiment of the present disclosure.
Figure 3:
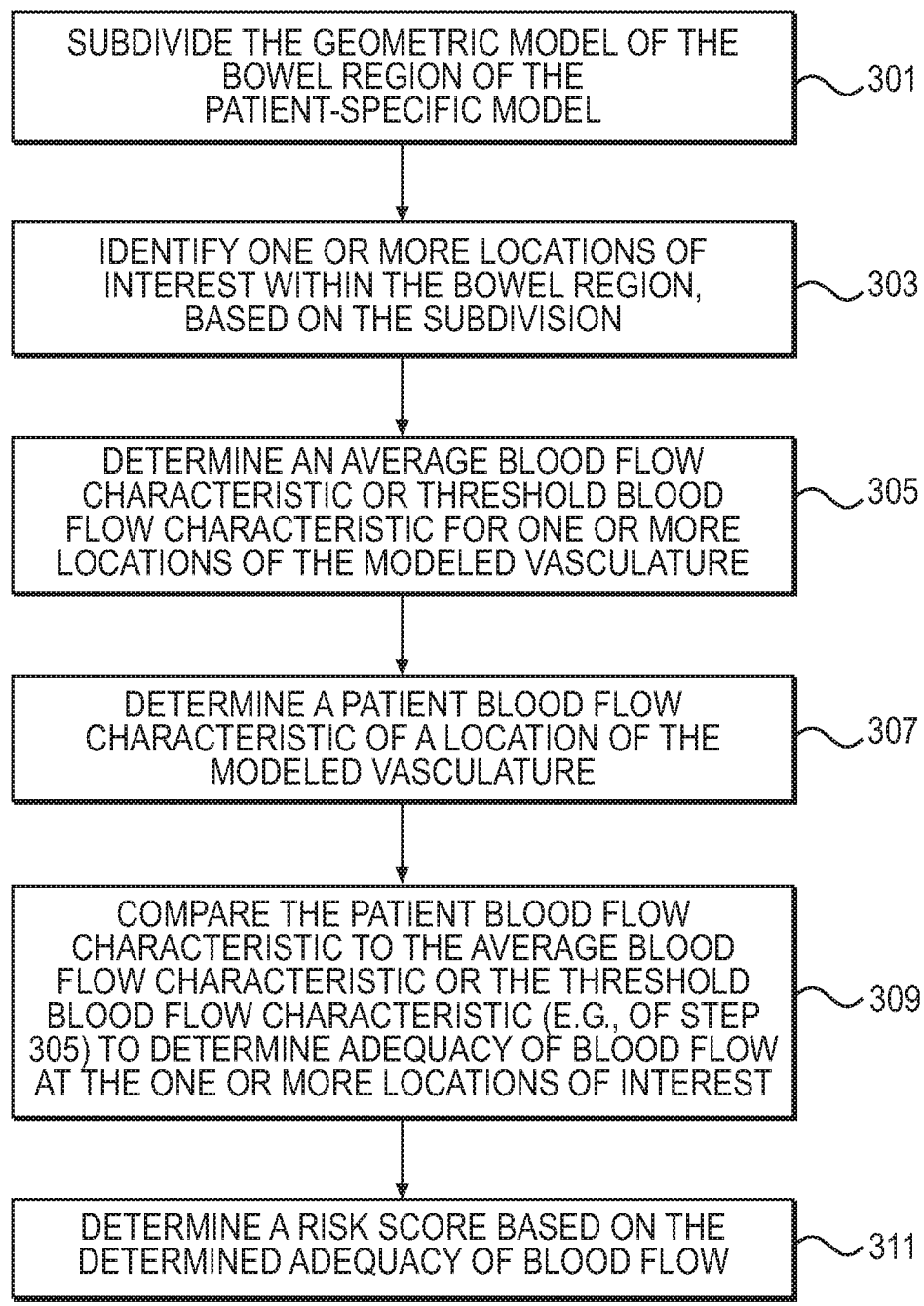
FIG. 3 is a flow diagram of an exemplary method of assessing blood supply adequacy to one or more locations of a patient's bowel, or risk to one or more regions of a patient's bowel, according to an exemplary embodiment of the present disclosure.
Figure 4:
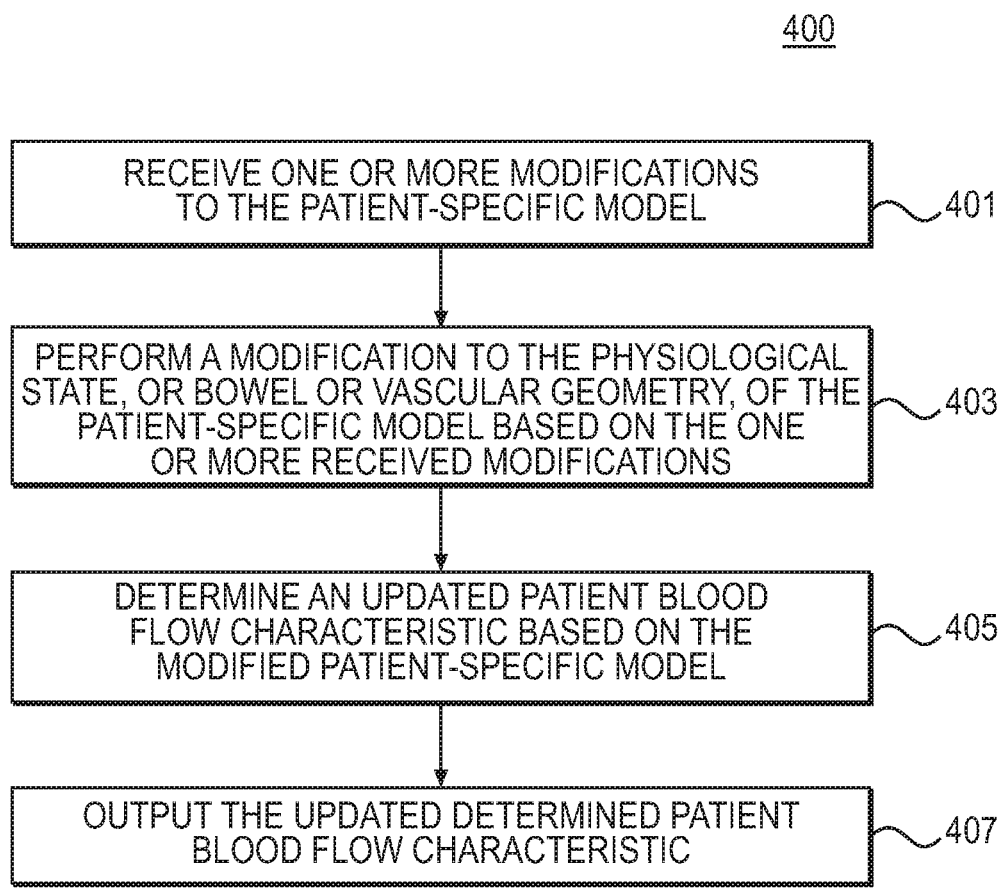
FIG. 4 is a flow diagram of an exemplary method of determining blood supply adequacy or risk, in response to one or more geometric changes to a patient's vascular model or changes in a patient's physiological state, according to an exemplary embodiment of the present disclosure.

FIGS. 2A-2C depict flowcharts of embodiments of methods for determining blood flow characteristics through a patient's visceral vasculature or bowel. FIG. 3 depicts a flowchart of a method for applying determined blood flow characteristics to disease assessment for a patient. In particular, FIG. 3 depicts a flowchart of a method for assessing blood supply adequacy to one or more locations of a patient's bowel, or risk to one or more regions of a patient's bowel, e.g., using determined blood flow characteristics through the patient's visceral vasculature or bowel. FIG. 4 depicts a flowchart of a method for treatment assessment and refined risk assessment. For example, FIG. 4 depicts a flowchart of a method for determining blood supply adequacy or risk, in response to one or more geometric changes to a patient's vascular model or modeled changes in a patient's physiological state. The modeled geometric changes may be based on or associated with one or more treatment options, e.g., modification of the vascular anatomy causing blockage (vascular recanalization, bypass or stenting) or removal of a portion of anatomy supplied by the vasculature (bowel resection, removal, bypass, etc.). The modeled change in physiological state may be associated with a treatment recommendation, e.g., a recommendation to avoid medications that cause a physiological state of increased blood flow or of constricted blood vessels. The modeled change in physiological state may also enhance risk assessment, e.g., an assessment indicating levels of activity that increase disease risk to a degree at which the patient should exercise caution. Techniques similar to those described in FIGS. 2A-4 may be applied to other areas of the body. For example, the techniques may be applied to evaluate a superior mesenteric artery obstruction or an obstruction of a celiac artery (including one or more of a hepatic, gastric, or splenic artery). Such an evaluation may provide predictions for a patient's likelihood of acute or chronic mesenteric ischemia (e.g., visceral angina or visceral ischemia). The techniques may also be applied to evaluate an inferior mesenteric artery obstruction, which may lead to ischemic colitis. The techniques may further be applied to evaluate mesenteric venous thrombosis, portal hypertension, etc.

FIG. 2A is a flow diagram of an exemplary method 200 of determining blood flow characteristics of blood flowing through a patient's visceral vasculature or bowel, according to an exemplary embodiment. The method of FIG. 2A may be performed by server systems 106, based on information, images, and data received from physicians 102 and/or third party providers 104 over electronic network 101.

In one embodiment, step 201 may include receiving a patient-specific anatomic model in an electronic storage medium of the server systems 106. Specifically, receiving the patient-specific anatomic model may include either generating the patient-specific anatomic model at the server system 106, or receiving one over an electronic network (e.g., electronic network 101) and/or an electronic storage medium (e.g., hard drive, network drive, smart phone, tablet, cloud drive, etc.). The patient-specific anatomic model may include at least a portion of the bowel of a specific patient and/or at least a portion of the patient visceral arterial vasculature. In one embodiment, the anatomic model may be derived from images of the person acquired via one or more available imaging or scanning modalities (e.g., computed tomography (CT) scans and/or magnetic resonance imaging (MRI)). The portion of the bowel included in the patient-specific anatomic model may include geometries of the patient's bowel regions, for example, one or more of the patient's illeum, jejunum, duodenum, large intestine, sigmoid colon, rectum, and/or appendix.

The patient visceral arterial vasculature of the patient-specific anatomic model may include a three-dimensional ("3D") geometrical model (e.g., a triangulated surface mesh, point cloud, etc.) of the arterial vasculature and/or a one-dimensional ("1D") geometrical model of the arterial vasculature. The patient-specific anatomic model may further include visceral vasculature, including one or more of the following: the patient's celiac artery, gastroduodenal artery, internal iliac artery, aorta, superior mesenteric artery ("SMA"), right colic artery, middle colic artery, jejunal and/or ileal branches, inferior pancreaticoduodenal artery, inferior mesenteric artery, left colic artery, superior sigmoid arteries, superior rectal artery, median sacral artery, venous vasculature, arteriovenous communication(s) in the mesenteric circulation (e.g., arteriovenous malformation ("AVM")), visceral aneurysm(s), dissection(s), etc. In one embodiment, a model may include a portion of the celiac artery that may branch into the patient's left gastric, splenic, and the common hepatic artery. Alternately or in addition, a model may include a portion of the patient's gastoduodenal artery, which may branch off the common hepatic artery and join the superior mesenteric artery ("SMA"), e.g., comprising a primary collateral pathway from the celiac artery to the SMA. The geometric model may also include a patient's internal iliac artery, especially when an internal iliac artery may be a primary collateral connection, e.g., in situations where the superior rectal artery may form an anastomosis to one or more branches of the internal iliac artery. Another model may include the aorta, for instance, for aortic ostial disease of one or more of the aortic branches. A model including venous vasculature may include one or more of a patient's portal vein and its branches, superior mesenteric vein, splenic vein, inferior mesenteric vein, etc.

In one embodiment, step 203 may include receiving a physiological state of the patient. Exemplary physiological states may include: rest, exercise, states of nutrition (e.g., fasting, different types and sizes of meals, etc.), hyperemia, postprandial states, etc. The patient's physiological state may impact calculations of blood flow characteristics, for instance, by affecting blood flow demand, microvascular resistance, blood flow rate, geometry of vasculature, vessel reactivity, etc. For example, a patient's tissue may have higher blood flow demand during an exercise state, than during a patient's resting state. Accounting for physiological state in determining a blood flow characteristic may provide greater context or accuracy in the resultant determined blood flow characteristic. In some embodiments, method 200 may be carried out at a set physiological state (e.g., baseline/resting physiological state or a patient's physiological state during imaging). In other embodiments, method 200 may include specifically receiving or identifying a physiological state of the patient at which to assess blood flow.

In one embodiment, step 205 may include determining, using a processor (e.g., a computer, laptop, tablet, smart phone, DSP, cloud computer, graphics processing unit, etc.), a blood flow characteristic at one or more locations in the patient-specific anatomic model (e.g., the patient-specific anatomic model including at least a portion of the patient visceral arterial vasculature). In some cases, the blood flow characteristic may be based on the received physiological state. The determination of the blood flow characteristic at one or more locations in the patient-specific anatomic model may be performed in several exemplary ways, as detailed in the methods included in FIGS. 2B and 2C. Examples of blood flow characteristics may include, for example: blood pressure, blood flow rate, fractional flow reserve (FFR), portal venous blood pressure, etc.

In one embodiment, step 207 may include outputting the blood flow characteristic to an electronic storage medium or display (e.g., a monitor, PDF, smart phone, tablet). For example, a display of step 207 may include an electronic visual representation of the model, including visual or numerical indicators showing the determined blood flow characteristic.

In one embodiment, step 209 may include receiving user interaction and updating the display based on the user interaction. For example, a user interaction may include a movement or gesture, movement of a pointer (e.g., a computer mouse), or scrolling function across a rendering of the patient-specific model. Step 209 may include, for example, showing a determined blood flow characteristic at a location associated with the movement, gesture, or mouse position, and updating the determined blood flow characteristic shown, as a movement, gesture, or mouse position corresponds to a different location on the rendered patient-specific model.

FIG. 2B is a flow diagram of an exemplary method 220 of determining a blood flow characteristic at one or more locations in a patient-specific vascular model using simulation, according to one embodiment. The method of FIG. 2B may be performed by server systems 106, based on information, images, and data received from physicians 102 and/or third party providers 104 over electronic network 101.

In one embodiment, the simulation of step 221 may include identifying an input location or region in the visceral vasculature and/or the portion of the bowel. In other words, step 221 may include identifying an area of interest at which a blood flow characteristic may be estimated.

In one embodiment, step 223 may include determining blood flow demand of the area of interest. For example, step 223 may include calculating a mass of the modeled bowel region to determine blood flow demand of the modeled bowel region and/or the area of interest (e.g., determined from step 221). For example, blood flow demand may be calculated based on an allometric relationship between total blood flow and tissue mass, e.g., resting flow ($Q_R$) is proportional to $mass^\beta$, where $\beta$ may be an empirically derived constant (e.g., in the 2-3 range). For instance, tissue mass of a modeled bowel region may be inferred from a patient's liver mass, where the liver mass may be derived from a CT scan. Step 223 may further include using the received physiological state to determine blood flow demand and/or to determine a value of microvascular resistance to use for the simulation. Resistance, e.g., vessel outlet resistance, may be set as: resistance (R) is proportional to the diameter of the outlet $(D_{outlet})^{(-\alpha)}$, where $\alpha$ may be an empirically derived constant (e.g., in the 2-3 range). The constant of proportionality may be changed to model various physiological states. For example, to model the change in a patient's physiological state from a resting state to a hyperemic (stress) state, the constant may be divided by 4, or any empirically measured value from known proportional relationships. The change in the constant of proportionality may vary based on the vessels being evaluated. For example, the relationship between resistance and the diameter of the outlet may vary between coronary arteries versus vessels of a bowel.

In one embodiment, step 225 may include determining boundary conditions at the blood flow input of the area of interest (e.g., of step 221). For example, step 225 may include determining boundary conditions by measuring aortic flow with MRI. Alternately or in addition, step 225 may include determining boundary conditions from an assumed pressure waveform (e.g., a constant pressure in the aorta or taking the aortic pressure as a function of measured blood pressure, for instance, brachial pressure). In one case, step 225 may include determining boundary conditions in the aorta using computations from one or more patient-specific models of abdominal aortic flow, or population-based models of abdominal aortic flow, and/or computations derived from literature.

In one embodiment, step 227 may include performing a 3D, 1D, or 0D (e.g., reduced order model) fluid simulation of blood flow in the modeled vasculature of at least the identified area of interest of the patient-specific model, for instance, given the microvascular resistance (e.g., from step 223) and/or boundary conditions (e.g., from step 225). In one embodiment, step 229 may include estimating a blood flow characteristic of at least the identified area of interest of the patient-specific model based on the simulation (e.g., from step 227).

FIG. 2C is a flow diagram of an exemplary method 240 of determining a blood flow characteristic at one or more locations in a patient-specific model using machine learning, according to one embodiment. The method of FIG. 2C may be performed by server systems 106, based on information, images, and data received from physicians 102 and/or third party providers 104 over electronic network 101.

For example, step 241 may include determining one or more locations in the modeled vasculature. For example, the locations may include locations distal to an observed disease. In heavily collateralized vasculature (e.g., visceral vasculature), particular locations related to disease may be difficult to discern. In such cases, the locations of step 241 may include all or a significant portion of modeled vasculature to determine if any obstructive disease may be observed. In one embodiment, step 243 may include determining one or more characteristics (or derived characteristics) of the modeled bowel and/or vasculature. Such characteristics may include, for instance, diameter or radius (of the vasculature), minimum proximal diameter or radius, proximal blood flow rate or pressure, mass of a bowel region supplied by a vessel of interest, overall mass of the patient's bowel region or at least a portion of the modeled bowel region, number of distal branches, number of proximal branches, physiological state of the patient, etc.

In one embodiment, step 245 may include identifying a database of patients, based on the patient. For example, step 245 may include receiving patient information (e.g., patient age, medical history, physiological state, characteristics from step 243, etc.) and selecting, from a variety of databases, a database containing patients with patient information that is similar to that of the patient. The database may include known or simulated examples of the blood flow characteristic. Such known or simulated examples of the blood flow characteristic may be associated with one or more other patients and/or a population-based study, for example.

In one embodiment, step 247 for a machine learning determination of a blood flow characteristic at the one or more locations may include assigning or interpolating the blood flow characteristic, using blood flow characteristic(s) in the database that are from vascular locations similar to or corresponding to the one or more locations.

In one embodiment, step 249 may include estimating a blood flow characteristic of the patient-specific model based on assessments from the assigning or interpolating (e.g., from step 227).

FIG. 3 is a flow diagram of an exemplary method 300 of assessing blood supply adequacy to one or more locations of a patient's bowel, and/or assessing risk to one or more regions of a patient's bowel, according to an exemplary embodiment. The method of FIG. 3 may be performed by server systems 106, based on information, images, and data received from physicians 102 and/or third party providers 104 over electronic network 101.

In one embodiment, method 300 may include subdividing a geometric model of a bowel region of the patient-specific model (step 301). For example, step 301 may include determining a standard subdivision and/or subdividing the geometric model of the bowel region while taking into account the blood flow characteristic analysis. For instance, step 301 may include presuming that blood supply to a tissue region of the geometric model is supplied by vessels proximate the tissue region. In such a case, step 301 may include subdividing the geometric model of the bowel region, at least in accordance to vessels touching or adjacent to the modeled bowel (e.g., assigning a location, or each location, in the bowel model to one or more vessels or vessel segments that are closest to the location).

In one embodiment, step 303 may include designating one or more locations of interest within the bowel region, based on the subdivision. For example, step 303 may include designating a subdivision (e.g., a region) of bowel tissue proximate a vessel as a location of interest.

Step 305 may include determining an average blood flow characteristic or predetermined threshold blood flow characteristic of one or more locations in the modeled vasculature. For example, a location in the modeled vasculature may have a healthy or average blood flow rate q, determined from a population-based measurement or estimate. Alternatively or in addition, q may be a predetermined threshold blood flow rate, where a patient blood flow rate below a given value of q may signify an inadequate blood supply to a respective tissue region of the patient. In one embodiment, the average blood flow characteristic or predetermined threshold blood flow characteristic may be associated with the one or more locations of interest within the bowel region (e.g., from step 303).

Step 307 may include assessing a patient blood flow characteristic at a location (e.g., using the methods of FIG. 2B or 2C) and/or receiving a patient blood flow characteristic (e.g., from the method of FIG. 2A) at a location of the modeled vasculature of the patient-specific model.

In one embodiment, step 309 may include determining adequacy of blood flow to at least one of the one or more locations of interest (e.g., from step 303). For example, step 309 may include comparing the patient blood flow characteristic against the predetermined threshold or average blood flow characteristic (e.g., from step 305). Based on the comparison, step 309 may include a making a determination of blood supply adequacy. For example, a patient blood flow rate below the predetermined threshold blood flow rate may be an indication that blood supply to the subdivision of interest in the modeled bowel region is inadequate. Method 300 may further include determining anomalous blood flow (e.g., from anomalous blood flow characteristic calculations) and inferring that tissue regions corresponding to the location (and distal locations) of the anomalous blood flow characteristic is inadequate. In one embodiment, step 309 may include outputting the determination of blood supply adequacy to an electronic storage medium and/or electronic display.

In addition, method 300 may include step 311 of determining a risk score for a patient condition, based on the blood supply adequacy (e.g., determined at step 309). For example, step 311 may include calculating a risk score for one or more conditions, including, ischemic colitis, abdominal pain (at rest or postprandial), gangrene, bowel perforation, sepsis, stricture, mesenteric ischemia, inflammatory conditions (e.g., ulcerative colitis, regional enteritis, acute or chronic mesenteric ischemia, mesenteric venous thrombosis, and/or portal hypertension), etc. Various conditions may be triggered by various levels of blood supply inadequacy. Step 311 may include determining patient risk for one or more conditions, e.g., based on blood supply adequacy at one or more locations in the modeled bowel.

FIG. 4 is a flow diagram of an exemplary method 400 of determining blood supply adequacy or risk, in response to one or more geometric changes to a patient's vascular model, or changes in a patient's physiological state, according to an exemplary embodiment. The method of FIG. 4 may be performed by server systems 106, based on information, images, and data received from physicians 102 and/or third party providers 104 over electronic network 101.

In one embodiment, method 400 may include receiving (e.g., from step 201) one or more modifications to the initial, received patient-specific model. For example, the modification may include a modeled treatment and/or a change in patient physiological state (step 401). Exemplary modifications may include changes to the patient-specific model that may reflect one or more treatments or disease progressions, for example, narrowing the patient-specific vascular model at a location to reflect disease progression, completely blocking the vascular model at one or more locations to reflect the onset or introduction of an occlusion or resection, widening the vascular model at a location to reflect disease regression, widening the vascular model at a location to reflect the introduction of a virtual stent, adding one or more additional branches to the vascular model to reflect the introduction of a bypass, etc. In one embodiment, the modification may be received via user input, for instance, from an interactive user interface that may include a rendering of the patient-specific model and/or computed blood flow characteristic(s).

In one embodiment, step 403 may include performing a modification to the patient-specific model to reflect at least one of the one or more received modifications. For example, step 403 may include determining a geometric change to the patient-specific model (e.g., of step 201) associated with the received modification or received treatment. For example, step 403 may include identifying a geometry of a treatment (e.g., a stent geometry) and modifying the patient-specific model based, at least in part, on the identified treatment geometry. In other words, step 403 may include updating or creating a new patient-specific model based on the one or more received modifications. In another embodiment, step 403 may include modifying the patient-specific model to reflect a change in physiological state.

In one embodiment, step 405 may include assessing (or reassessing) a blood flow characteristic, the determination of blood supply adequacy, and/or risk, given the modified patient-specific model. For example, step 405 may include updating boundary conditions or other parameters, given the modifications, and estimating a blood flow characteristic of the patient (e.g., using methods of FIG. 2B or 2C).

In one embodiment, step 407 may include outputting the reassessment of the patient blood flow characteristic to an electronic storage medium or electronic display. In one embodiment, the output may include an interface that may permit a user to see fluctuations in the patient blood flow characteristic, given disease progression and/or through a cycle of physiological state change. For example, a user may select a time-varying display that may show disease progression through changes in the patient-specific geometric model while also showing blood flow characteristic response to the progression. In one embodiment, several types of blood flow characteristics (and their changes) may be shown at one time. For example, a display may include a table or chart including several types of blood flow characteristics and the estimates of the blood flow characteristics may be charted or displayed for a time-varying simulation including various stages of disease, treatment, and/or physiological state change. In one embodiment, step 407 may further include providing a physiological state recommendation or recommending a maximum physiological state (e.g., exercise level or physical activity intensity level) in which a patient can engage in, based on adequacy of blood flow supply while the patient's body is at various physiological states.

Inadequate blood supply in visceral vasculature of the bowel may cause various harmful health conditions, including visceral ischemia and related disorders. Such conditions are often difficult to diagnose because the conditions may only be expressed at certain physiological states, and because the high amount of collateralization in visceral vasculature may interfere with the ability to determine functional significance of vascular disease in the visceral vasculature. One such condition is ischemic colitis, which is especially difficult to diagnose and differentiate from other causes of abdominal pain. The systems and methods described provide for assessing blood supply in the visceral vasculature and identifying functional significance of disease in the visceral vasculature (e.g., based on the blood supply assessment). In determining the functional significance of disease, the systems and methods described also improve diagnoses and treatment planning for visceral ischemia and related disorders where collateralization may complicate diagnoses.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of assessment of ischemia and related disorders, the method comprising:
   receiving a non-invasive patient-specific three dimensional anatomic model including a portion of a patient's bowel;
   receiving a patient physiological state, the physiological state being a state different from a resting state;
   determining a blood flow demand of the portion of the patient's bowel modeled by the non-invasive patient-specific three dimensional anatomic model, based on a determined mass of the portion of the patient's bowel and the received physiological state of the patient;
   performing a fluid simulation of a blood flow in the received patient-specific three dimensional anatomic model;
   determining a blood flow characteristic of blood delivered to the portion of the patient's bowel using the fluid simulation, the determined blood flow demand, and a value of microvascular resistance based on the received physiological state;
   determining adequacy of blood flow to the portion of the patient's bowel by comparing the determined blood flow characteristic with a threshold blood flow characteristic; and
   generating and displaying (i) an assessment of blood supply adequacy based on the determined adequacy of blood flow, or (ii) a risk score defining a risk of disease of the patient's bowel, based on the comparison.

2. The computer-implemented method of claim 1, wherein the blood flow characteristic includes one or more of blood pressure, flow rate, fractional flow reserve, or portal venous pressure.

3. The computer-implemented method of claim 1, further comprising:
   determining the blood flow demand based on an allometric relationship between blood flow and the determined mass of the portion of the patient's bowel.

4. The computer-implemented method of claim 3, further including:
   subdividing the non-invasive patient-specific three dimensional anatomic model into one or more bowel regions;
   determining an association between a vessel of the patient's vasculature and at least one bowel region of the one or more bowel regions; and
   determining blood flow adequacy for one or more locations of the portion of the patient's bowel distal to the at least one bowel region, based on a determined blood flow adequacy for the at least one bowel region.

5. The computer-implemented method of claim 1, further comprising:
   calculating the blood flow characteristic using a fluid simulation or using blood flow characteristics based on one or more other patients.

6. The computer-implemented method of claim 1, wherein the value of microvascular resistance comprises resistance at a vessel outlet.

7. The computer-implemented method of claim 6, further comprising:
   modifying a geometry of the non-invasive patient-specific three dimensional anatomic model;
   determining a modified blood flow characteristic at a location in the modified non-invasive patient-specific three dimensional anatomic model based on the modified non-invasive patient-specific three dimensional anatomic model; and
   generating an updated assessment or display of blood supply adequacy to the patient's bowel, or
   generating or displaying a risk score for risk of disease to one or more regions of the patient's bowel, based on the determined modified blood flow characteristic at the location in the modified non-invasive patient-specific three dimensional anatomic model.

8. The computer-implemented method of claim 1, further comprising:
   determining the risk score for risk of disease to one or more regions of the patient's bowel based on the assessment of blood supply adequacy to the patient's bowel, wherein the risk of disease includes risk of one or more of mesenteric ischemia, intestinal ischemia, ischemic colitis, abdominal pain, gangrene, bowel perforation, sepsis, stricture, and inflammatory conditions.

9. A system for assessment of ischemia and related disorders, the system comprising:
   at least one data storage device storing instructions for assessment of ischemic colitis; and
   at least one processor configured to execute the instructions to perform a method including:
      receiving a non-invasive patient-specific three dimensional anatomic model including a portion of a patient's bowel;
      receiving a patient physiological state, the physiological state being a state different from a resting state;
      determining a blood flow demand of the portion of the patient's bowel modeled by the non-invasive patient-specific three dimensional anatomic model, based on a determined mass of the portion of the patient's bowel and the received physiological state of the patient;
      performing a fluid simulation of a blood flow in the received patient-specific three dimensional anatomic model;
      determining a blood flow characteristic of blood delivered to the portion of the patient's bowel using the fluid simulation, the determined blood flow demand, and a value of microvascular resistance based on the received physiological state;

determining adequacy of blood flow to the portion of the patient's bowel by comparing the determined blood flow characteristic with a threshold blood flow characteristic; and generating and displaying (i) an assessment of blood supply adequacy based on the determined adequacy of blood flow, or (ii) a risk score defining a risk of disease of the patient's bowel, based on the comparison.

10. The system of claim 9, wherein the blood flow characteristic includes one or more of blood pressure, flow rate, fractional flow reserve, or portal venous pressure.

11. The system of claim 9, wherein the system is further configured for:

determining the blood flow demand based on an allometric relationship between blood flow and the determined mass of the portion of the patient's bowel.

12. The system of claim 11, wherein the system is further configured for:

subdividing the non-invasive patient-specific three dimensional anatomic model into one or more bowel regions;

determining an association between a vessel of the patient's vasculature and at least one bowel region of the one or more bowel regions; and determining blood flow adequacy for one or more locations of the portion of the patient's bowel distal to the at least one bowel region, based on a determined blood flow adequacy for the at least one bowel region.

13. The system of claim 9, wherein the system is further configured for:

calculating the blood flow characteristic using a fluid simulation or using blood flow characteristics based on one or more other patients.

14. The system of claim 9, wherein the value of microvascular resistance comprises resistance at a vessel outlet.

15. The system of claim 14, wherein the system is further configured for:

modifying a geometry of the non-invasive patient-specific three dimensional anatomic model;

determining a modified blood flow characteristic at a location in the modified non-invasive patient-specific three dimensional anatomic model based on the modified non-invasive patient-specific three dimensional anatomic model; and generating an updated assessment or display of blood supply adequacy to the patient's bowel, or generating or displaying a risk score for risk of disease to one or more regions of the patient's bowel, based on the determined modified blood flow characteristic at the location in the modified non-invasive patient-specific three dimensional anatomic model.

16. The system of claim 9, wherein the system is further configured for:

determining the risk score for risk of disease to one or more regions of the patient's bowel based on the assessment of blood supply adequacy to the patient's bowel, wherein the risk of disease may include risk of one or more of ischemic colitis, abdominal pain, gangrene, bowel perforation, sepsis, stricture, mesenteric ischemia, and inflammatory conditions.

17. A non-transitory computer readable medium for use on a computer system containing computer-executable programming instructions for performing a method of assessment of ischemia and related disorders, the method comprising:

receiving a non-invasive patient-specific three dimensional anatomic model including a portion of a patient's bowel;

receiving a patient physiological state, the physiological state being a state different from a resting state;

determining a blood flow demand of the portion of the patient's bowel modeled by the non-invasive patient-specific three dimensional anatomic model, based on a determined mass of the portion of the patient's bowel and the received physiological state of the patient;

performing a fluid simulation of a blood flow in the received patient-specific three dimensional anatomic model;

determining a blood flow characteristic of blood delivered to the portion of the patient's bowel using the fluid simulation, the determined blood flow demand, and a value of microvascular resistance based on the received physiological state;

determining adequacy of blood flow to the portion of the patient's bowel by comparing the determined blood flow characteristic with a threshold blood flow characteristic; and generating and displaying (i) an assessment of blood supply adequacy based on the determined adequacy of blood flow, or (ii) a risk score defining a risk of disease of the patient's bowel based on the comparison.

18. The non-transitory computer readable medium of claim 17, wherein the blood flow characteristic includes one or more of blood pressure, flow rate, fractional flow reserve, or portal venous pressure.

19. The non-transitory computer readable medium of claim 17, the method further comprising:

determining the blood flow demand based on an allometric relationship between blood flow and the determined mass of the portion of the patient's bowel.

20. The non-transitory computer readable medium of claim 19, the method further comprising:

subdividing the non-invasive patient-specific three dimensional anatomic model into one or more bowel regions;

determining an association between a vessel of the patient's vasculature and at least one bowel region of the one or more bowel regions; and determining blood flow adequacy for one or more locations of the portion of the patient's bowel distal to the at least one bowel region, based on a determined blood flow adequacy for the at least one bowel region.

* * * * *